United States Patent
Raman et al.

(10) Patent No.: US 9,796,658 B2
(45) Date of Patent: Oct. 24, 2017

(54) PRODUCTION AND PURIFICATION OF ESTERS OF POLYUNSATURATED FATTY ACIDS

(71) Applicant: DSM IP Assets B.V., Te Heerlen (NL)

(72) Inventors: Krishna Raman, Wilmington, DE (US); Jung Lee, McLean, VA (US); Neil Leininger, Winchester, KY (US); Chris Luigart, Lexington, KY (US)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 14/154,140

(22) Filed: Jan. 13, 2014

(65) Prior Publication Data

US 2014/0128465 A1     May 8, 2014

Related U.S. Application Data

(63) Continuation of application No. 12/163,555, filed on Jun. 27, 2008, now abandoned.

(60) Provisional application No. 60/947,284, filed on Jun. 29, 2007.

(51) Int. Cl.

| | | |
|---|---|---|
| *C07C 69/587* | (2006.01) | |
| *A21D 2/16* | (2006.01) | |
| *C07C 67/03* | (2006.01) | |
| *C07C 67/08* | (2006.01) | |
| *C11C 3/00* | (2006.01) | |
| *C07C 67/60* | (2006.01) | |
| *A23K 20/158* | (2016.01) | |

(52) U.S. Cl.
CPC .............. *C07C 69/587* (2013.01); *A21D 2/16* (2013.01); *A23K 20/158* (2016.05); *C07C 67/03* (2013.01); *C07C 67/08* (2013.01); *C07C 67/60* (2013.01); *C11C 3/003* (2013.01)

(58) Field of Classification Search
None
See application file for complete search history.

(56) References Cited

U.S. PATENT DOCUMENTS

| | | | | |
|---|---|---|---|---|
| 5,658,767 | A * | 8/1997 | Kyle | ............................. 435/134 |
| 6,313,330 | B1 | 11/2001 | Kiyohara et al. | |
| 6,395,778 | B1 * | 5/2002 | Luthria | ................... C11B 1/025 |
| | | | | 514/549 |
| 6,677,145 | B2 * | 1/2004 | Mukerji et al. | ............... 435/193 |
| 2003/0161864 | A1 * | 8/2003 | Tanaka et al. | ................. 424/439 |
| 2004/0106584 | A1 * | 6/2004 | Arterburn et al. | ............ 514/165 |
| 2004/0162437 | A1 * | 8/2004 | Fabritius et al. | .............. 554/191 |
| 2004/0266874 | A1 * | 12/2004 | Akimoto | ................... A23D 9/00 |
| | | | | 514/560 |
| 2005/0129831 | A1 * | 6/2005 | Fabritius | .................. A23D 9/00 |
| | | | | 426/607 |

FOREIGN PATENT DOCUMENTS

| | | | | |
|---|---|---|---|---|
| WO | WO1989011521 | 11/1989 | | |
| WO | WO200073254 | 12/2000 | | |
| WO | WO 2004/028529 | * 4/2004 | ........... A61K 31/202 | |
| WO | WO 2006/017692 | * 2/2006 | ........... A61K 31/192 | |
| WO | WO2006079533 | 8/2006 | | |

OTHER PUBLICATIONS

Huang, J. et al., Enzymatic Preparation of Glycerides rich in Docosahexaenoic acid from Thraustochytrid Single Cell oils by Candida rugosa Lipase, 2002, Journal of Oleo Science, vol. 51, No. 7, pp. 447-455.*

Jiang, Y. et al., Fatty acid composition and squalene content of marine microalga Schizochytrium mangrovei, 2004, Journal of Agricultural and Food Chemimstry, vol. 52, No. 5, pp. 1196-1200.*

Sing, A. et al., Docosapentaenoic acid (C22:5, omega-3) production by Phythium acanthicum, 1998, Journal of Industrial Microbiology & Biotechnology, vol. 20, pp. 187-191.*

Higashiyama, K., et al., Production of Arachidonic acid by Mortierella Fungi, 2002, Biotechnol. Bioprocess Eng., vol. 7, No. 5, pp. 252-262.*

Shimada, Y. et al., Enrichment of Arachidonic acid: Selective hydrolysis of a single-cell oil form Mortierella with Candid Cylindracea Lipase, 1995, JAOCS, vol. 72, No. 11, pp. 1323-1327.*

Mansour, M.P., et al., Lipid and fatty acid yield of nine stationary-phase microalgae: Applications and unusual C24-C28 polyunsaturated fatty acids, 2005, Journal of Applied Phycology, vol. 17, pp. 287-300.*

* cited by examiner

*Primary Examiner* — Yate K Cutliff
(74) *Attorney, Agent, or Firm* — Xi Chen; Shannon McGarrah

(57) ABSTRACT

The present invention includes methods for producing and purifying esters of polyunsaturated fatty acids that include reacting a composition having triglycerides with polyunsaturated fatty acid residues in the presence of an alcohol and a base to produce an ester of a polyunsaturated fatty acid from the triglycerides. The composition can be a polyunsaturated fatty acid-containing composition that has not been conventionally processed. The reacted composition can be further processed by distillation.

6 Claims, No Drawings

PRODUCTION AND PURIFICATION OF ESTERS OF POLYUNSATURATED FATTY ACIDS

CROSS REFERENCE TO RELATED APPLICATION

This application is a continuation of U.S. patent application Ser. No. 12/163,555, which claims the benefit of priority under 35 U.S.C. §119(e) of U.S. Provisional Application No. 60/947,284, filed Jun. 29, 2007, the disclosure of which is incorporated by reference herein in its entirety.

FIELD OF THE INVENTION

The invention relates to methods for producing and purifying esters of polyunsaturated fatty acids from triglyceride containing compositions. The invention also relates to compositions comprising polyunsaturated fatty acids.

BACKGROUND OF THE INVENTION

It is desirable to increase the dietary intake of many beneficial nutrients. Particularly beneficial nutrients include fatty acids such as omega-3 and omega-6 long chain polyunsaturated fatty acids (LC-PUFAs) and esters thereof. Omega-3 PUFAs are recognized as important dietary compounds for preventing arteriosclerosis and coronary heart disease, for alleviating inflammatory conditions and for retarding the growth of tumor cells. Omega-6 PUFAs serve not only as structural lipids in the human body, but also as precursors for a number of factors in inflammation, such as prostaglandins and leukotrienes. Long chain omega-3 and the omega-6 PUFAs represent important classes of PUFAs.

There are two main series or families of LC-PUFAs, depending on the position of the double bond closest to the methyl end of the fatty acid: the omega-3 series contains a double bond at the third carbon, while the omega-6 series has no double bond until the sixth carbon. Thus, docosahexaenoic acid ("DHA") has a chain length of 22 carbons with 6 double bonds beginning with the third carbon from the methyl end and is designated "22:6 n-3". Other important omega-3 LC-PUFAs include eicosapentaenoic acid ("EPA"), which is designated "20:5 n-3," and omega-3 docosapentaenoic acid ("DPA n-3"), which is designated "22:5 n-3." Important omega-6 LC-PUFAs include arachidonic acid ("ARA"), which is designated "20:4 n-6," and omega-6 docosapentaenoic acid ("DPA n-6"), which is designated "22:5 n-6."

Because humans and many other animals cannot directly synthesize omega-3 and omega-6 essential fatty acids, they must be obtained in the diet. Traditional dietary sources of PUFAs include vegetable oils, marine animal oils, fish oils and oilseeds. In addition, oils produced by certain microorganisms have been found to be rich in LC-PUFAs. The oils derived from each of these sources, however, also contain substantial levels of saturated fatty acids and other undesirable impurities.

Numerous methods have been used to isolate or purify PUFAs and derivatives thereof from crude oils. Among these processes are fractional crystallization at low temperatures, urea adduct crystallization, extraction with metal salt solutions, super critical fluid fractionation on countercurrent columns and high performance liquid chromatography.

The increased use of PUFAs and esters thereof in the fields of medicine and nutrition has created a commensurate need for PUFAs that are concentrated and free of impurities. Previous efforts directed to purifying PUFAs, however, have suffered from problems such as high costs and decreased yields due, in part, to the use of harsh reagents. Accordingly, there is a need for improved methods of isolating and purifying PUFAs in a form that can be consumed and utilized by humans and other animals.

SUMMARY OF THE INVENTION

The present invention provides a method for purifying a composition comprising triglycerides having polyunsaturated fatty acid residues comprising reacting the composition in the presence of an alcohol and a base to produce an ester of a polyunsaturated fatty acid from the triglycerides and distilling the composition to recover a fraction comprising the ester of the polyunsaturated fatty acid.

In some embodiments, the step of reacting the composition in the presence of an alcohol and a base is performed at a temperature from about 60° C. to about 120° C.

In some embodiments, the step of reacting the composition in the presence of an alcohol and a base is performed for a time from about 2 hours to about 12 hours.

In some embodiments, the composition comprising triglycerides having polyunsaturated fatty acid residues has not been subjected to one or more treatments selected from the group consisting of refining, desolventization, deodorization, winterization, chill filtration, and bleaching.

In some embodiments, the composition comprising triglycerides having polyunsaturated fatty acid residues has not been subjected to refining, desolventization, deodorization, winterization, chill filtration, and bleaching.

In some embodiments, the composition comprising triglycerides having polyunsaturated fatty acid residues is from a source selected from the group consisting of a plant, a microorganism, an animal, and mixtures of the foregoing.

In some embodiments, the source is a microorganism selected from the group consisting of algae, bacteria, fungi and protists.

In some embodiments, the source is selected from the group consisting of plants selected from the group consisting of soybean, corn, rice, safflower, sunflower, canola, flax, peanut, mustard, rapeseed, chickpea, cotton, lentil, white clover, olive, palm, borage, evening primrose, linseed and tobacco and mixtures thereof.

In some embodiments, the source is selected from the group consisting of a genetically modified plant and a genetically modified microorganism, wherein the genetic modification comprises the introduction of polyketide synthase genes.

In some embodiments, the source is a microorganism selected from the group consisting of Thraustochytriales, dinoflagellates, and *Mortierella*.

In some embodiments, the microorganism is Thraustochytriales, *Schizochytrium* or *Thraustochytrium*.

In some embodiments, the microorganism is a dinoflagellate of the genus *Crypthecodinium*.

In some embodiments, the source is an animal selected from aquatic animals.

In some embodiments, the polyunsaturated fatty acid is a polyunsaturated fatty acid having a chain length of at least 18 carbons.

In some embodiments, the polyunsaturated fatty acid is a polyunsaturated fatty acid selected from the group consisting of docosahexaenoic acid, docosapentaenoic acid, arachidonic acid, eicosapentaenoic acid, stearidonic acid, linolenic acid, alpha linolenic acid, gamma linolenic acid, conjugated linolenic acid and mixtures thereof.

In some embodiments, the polyunsaturated fatty acid is docosahexaenoic acid.

In some embodiments, the polyunsaturated fatty acid is arachadonic acid.

In some embodiments, the base is a base of the formula RO-M, wherein M is a monovalent cation and RO is an alkoxide of a $C_{1-6}$ alkyl alcohol.

In some embodiments, the base is sodium ethoxide.

In some embodiments, the alcohol is a $C_{1-6}$ alkyl alcohol.

In some embodiments, the alcohol is ethanol and the ester is an ethyl ester of the polyunsaturated fatty acid.

In some embodiments, the step of distilling the composition to recover a fraction comprising the ester of the polyunsaturated fatty acid is performed under vacuum.

In some embodiments, the step of distilling the composition to recover a fraction comprising the ester of the polyunsaturated fatty acid is performed at a temperature of less than about 170° C.

In some embodiments, the fraction recovered comprises at least about 50 wt. %, 75 wt. %, 90 wt. %, or 95 wt. % ester of the polyunsaturated fatty acid.

In some embodiments, the step of reacting the composition in the presence of an alcohol and a base produces an ester of a polyunsaturated fatty acid from the triglycerides by direct transesterification.

In some embodiments, the method further comprises a) combining the fraction comprising the ester of the polyunsaturated fatty acid with urea in a medium; b) cooling or concentrating the medium to form a urea-containing precipitate and a liquid fraction; and c) separating the precipitate from the liquid fraction.

In some embodiments, the medium further comprises an organic solvent that can solubilize the ester of the polyunsaturated fatty acid.

In some embodiments, the organic solvent comprises an alkyl alcohol comprising from 1 to 4 carbon atoms.

In some embodiments, the organic solvent comprises ethanol.

In some embodiments, the medium is cooled to a temperature of from about 0° C. to about 25° C. to form the urea-containing precipitate.

In some embodiments, at least a portion of the urea-containing precipitate is formed under a non-oxidizing atmosphere.

The present invention also provides a method for producing an ester of a polyunsaturated fatty acid from a composition comprising triglycerides having polyunsaturated fatty acid residues comprising transesterifying the composition in the presence of an alcohol and a base to produce an ester of the polyunsaturated fatty acid from the triglycerides and distilling the composition to recover a fraction comprising the ester of the polyunsaturated fatty acid.

The present invention further provides a method for purifying a composition comprising triglycerides having polyunsaturated fatty acid residues comprising reacting the composition in the presence of an alcohol and a base to produce an ester of the polyunsaturated fatty acid from the triglycerides and separating a fraction comprising at least about 75% ester of the polyunsaturated fatty acid.

In some embodiments, the step of separating comprises distilling.

The present invention also provides a method for preparing a composition comprising an ester of a polyunsaturated fatty acid comprising reacting a composition comprising triglycerides having polyunsaturated fatty acid residues in the presence of an alcohol and a base to produce an ester of a polyunsaturated fatty acid from the triglycerides, wherein the composition comprising triglycerides having polyunsaturated fatty acid residues has not been subjected to one or more treatments selected from the group consisting of refining, desolventization, deodorization, winterization, chill filtration, and bleaching.

In some embodiments, the step of reacting the composition in the presence of an alcohol and a base is performed at a temperature from about 60° C. to about 120° C.

In some embodiments, the step of reacting the composition in the presence of an alcohol and a base is performed for a time from about 2 hours to about 12 hours.

In some embodiments, the method further comprises a step of distilling the composition to recover a fraction comprising the ester of the polyunsaturated fatty acid.

In some embodiments, the composition comprising triglycerides having polyunsaturated fatty acid residues is from a source selected from the group consisting of a plant, a microorganism, an animal, and mixtures of the foregoing.

In some embodiments, the source is a microorganism selected from the group consisting of algae, bacteria, fungi and protists.

In some embodiments, the source is selected from the group consisting of plants selected from the group consisting of soybean, corn, rice, safflower, sunflower, canola, flax, peanut, mustard, rapeseed, chickpea, cotton, lentil, white clover, olive, palm, borage, evening primrose, linseed and tobacco and mixtures thereof.

In some embodiments, the source is selected from the group consisting of a genetically modified plant and a genetically modified microorganism, wherein the genetic modification comprises the introduction of polyketide synthase genes.

In some embodiments, the source is a microorganism selected from the group consisting of Thraustochytriales, dinoflagellates, and *Mortierella*.

In some embodiments, the source is a microorganism selected from the group consisting of Thraustochytriales, dinoflagellates, and *Mortierella*.

In some embodiments, the microorganism is a dinoflagellate of the genus *Crypthecodinium*.

In some embodiments, the source is an animal selected from aquatic animals.

In some embodiments, the polyunsaturated fatty acid is a polyunsaturated fatty acid having a chain length of at least 18 carbons.

In some embodiments, the polyunsaturated fatty acid is a polyunsaturated fatty acid selected from the group consisting of docosahexaenoic acid, docosapentaenoic acid, arachidonic acid, eicosapentaenoic acid, stearidonic acid, linolenic acid, alpha linolenic acid, gamma linolenic acid, conjugated linolenic acid and mixtures thereof.

In some embodiments, the polyunsaturated fatty acid is docosahexaenoic acid.

In some embodiments, the polyunsaturated fatty acid is arachadonic acid.

In some embodiments, the base is a base of the formula RO-M, wherein M is a monovalent cation and RO is an alkoxide of a $C_{1-6}$ alkyl alcohol.

In some embodiments, the base is sodium ethoxide.

In some embodiments, the alcohol is a $C_{1-6}$ alkyl alcohol.

In some embodiments, the alcohol is ethanol and the ester is an ethyl ester of the polyunsaturated fatty acid.

In some embodiments, the step of distilling the composition to recover a fraction comprising the ester of the polyunsaturated fatty acid is performed under vacuum.

In some embodiments, the step of distilling the composition to recover a fraction comprising the ester of the polyunsaturated fatty acid is performed at a temperature of less than about 170° C.

In some embodiments, the fraction recovered comprises at least about 50 wt. %, 75 wt. %, 90 wt. %, or 95 wt. % ester of the polyunsaturated fatty acid.

In some embodiments, the step of reacting the composition in the presence of an alcohol and a base produces an ester of a polyunsaturated fatty acid from the triglycerides by direct transesterification.

The present invention also provides a composition comprising at least about 90 wt. % ethyl ester of docosahexaenoic acid, wherein the composition further comprises at least about 0.1 wt. % of 4, 7, 10, 13, 16, 19, 22, 25 octacosaoctaenoic acid (C28:8) or an ester thereof.

In some embodiments, the composition comprises at least about 0.5 wt. %, 1.0 wt. %, or 1.2 wt. % of 4, 7, 10, 13, 16, 19, 22, 25 octacosaoctaenoic acid (C28:8) or an ester thereof.

In some embodiments, the composition further comprises at least about 0.1 wt. %, 0.3 wt. %, 0.4 wt. %, or 0.5 wt. % of docosapentaenoic acid (n-3) or an ester thereof.

In some embodiments, the composition comprises at least about 92 wt. % or 95 wt. % ethyl ester of docosahexaenoic acid.

In some embodiments, the composition further comprises less than about 1 wt. %, 0.5 wt. % or 0.25 wt. % eicosapentaenoic acid or an ester thereof.

The present invention further provides a composition comprising at least about 90 wt. % ethyl ester of docosahexaenoic acid, wherein the composition further comprises at least about 0.1 wt. % of docosapentaenoic acid (n-3) or an ester thereof.

In some embodiments, the composition comprises at least about 0.3 wt. %, 0.4 wt. %, or 0.5 wt. % of docosapentaenoic acid (n-3) or an ester thereof.

In some embodiments, the composition further comprises at least about 0.5 wt. %, 0.75 wt. %, 1.0 wt. %, or 1.2 wt. % of 4, 7, 10, 13, 16, 19, 22, 25 octacosaoctaenoic acid (C28:8) or an ester thereof.

In some embodiments, the composition comprises at least about 92 wt. % or 95 wt. % ethyl ester of docosahexaenoic acid.

In some embodiments, the composition further comprises less than about 1 wt. %, 0.5 wt. % or 0.25 wt. % eicosapentaenoic acid or an ester thereof.

The present invention also provides a composition comprising at least about 90 wt. % ethyl ester of docosahexaenoic acid, wherein the composition further comprises at least one additional fatty acid or an ester thereof with a boiling point of about 150-170° C. at a pressure of 0.8 mm Hg.

The present invention further provides a composition comprising at least about 70 wt. % ethyl ester of docosahexaenoic acid and at least about 25 wt. % ethyl ester of docosapentaenoic acid (n-6).

In some embodiments, the composition further comprises less than about 4% of a saturated fatty acid or an ester thereof.

In some embodiments, the saturated fatty acid or an ester thereof contains less than 20 carbons.

In some embodiments, the saturated fatty acid or an ester thereof contains 14 or 16 carbons.

The present invention also provides a composition comprising at least about 90 wt. % of a combination of ethyl ester of docosahexaenoic acid and ethyl ester of docosapentaenoic acid (n-6).

In some embodiments, the composition comprises at least about 10 wt. % ethyl ester of docosahexaenoic acid and at least about 10 wt. % ethyl ester of docosapentaenoic acid (n-6).

In some embodiments, the composition further comprises less than about 4% of a saturated fatty acid or an ester thereof.

In some embodiments, the saturated fatty acid or an ester thereof contains less than 20 carbons.

In some embodiments, the saturated fatty acid or an ester thereof contains 14 or 16 carbons.

The present invention further provides a comprising at least about 90 wt. % of a combination of ethyl ester of docosahexaenoic acid and ethyl ester of docosapentaenoic acid (n-6), wherein the composition further comprises at least one additional fatty acid or an ester thereof with a boiling point of about 150-175° C. at a pressure of 0.5 mm Hg.

The present invention also provides a method for preparing a composition comprising an ester of a polyunsaturated fatty acid comprising reacting a composition comprising triglycerides having polyunsaturated fatty acid residues in the presence of an alcohol and a base to produce an ester of a polyunsaturated fatty acid from the triglycerides, wherein the composition comprising triglycerides having polyunsaturated fatty acid residues comprises at least one characteristic selected from the group consisting of: at least about 300 ppm phosphorus, at least about 0.4% free fatty acids, and a peroxide value of at least about 0.2 meq/kg.

The present invention also provides a method for purifying a composition comprising triglycerides having polyunsaturated fatty acid residues, wherein the composition comprises at least one characteristic selected from the group consisting of: at least about 300 ppm phosphorus, at least about 0.4% free fatty acids, and a peroxide value of at least about 0.2 meq/kg, comprising a) reacting the composition in the presence of an alcohol and a base to produce an ester of a polyunsaturated fatty acid from the triglycerides; and b) distilling the composition to recover a fraction comprising the ester of the polyunsaturated fatty acid.

The present invention further provides a composition comprising at least about 60 wt. % esters of arachidonic acid.

In some embodiments, the composition further comprises less than about 10 wt. % eicosapentaenoic acid.

In some embodiments, the esters of arachidonic acid are ethyl esters of arachidonic acid.

The present invention also provides a method of treating a subject with high levels of triglycerides comprising administering one of the above described compositions to the subject.

The present invention further provides a method of treating a subject with a neurological disorder, dementia or a pre-dementia related condition comprising administering one of the above described compositions to the subject.

DESCRIPTION OF THE INVENTION

The present invention provides novel methods for the purification of compositions containing triglycerides having PUFA residues. In various aspects, the invention includes reacting the composition in the presence of an alcohol and a base to produce an ester of a polyunsaturated fatty acid from the triglycerides. In one embodiment, the invention advantageously and efficiently is conducted on relatively crude oils that have not been subjected to conventional processing methods that can include refining, bleaching, deodorizing and winterization. In another embodiment, the invention includes producing esters from triglycerides and then distilling the resulting composition to recover a fraction comprising the ester of the polyunsaturated fatty acid. In an additional embodiment, the fraction comprising the ester of the polyunsaturated fatty acid is further purified by urea crystallization. The present invention allows the efficient and cost effective production of esters of PUFAs directly from crude or processed oils.

The starting material for the methods of the present invention is a composition comprising triglycerides having PUFA residues. The terms "oils" and "compositions comprising triglycerides having PUFA residues" are used interchangeably throughout this application. As used herein, a "triglyceride" is an ester of three fatty acid residues and glycerol having a general chemical formula of $CH_2(OOCR^1)CH(OOCR^2)CH_2(OOCR^3)$, wherein each of $OOCR^1$, $OOCR^2$, and $OOCR^3$ represents a fatty acid residue. Suitable triglycerides contain at least one PUFA. In some embodiments, the PUFA has a chain length of at least 18 carbons. Such PUFAs are referred to herein as long chain PUFAs or LC PUFAs. In some embodiments, the PUFA can be docosahexaenoic acid C22:6 n-3 (DHA), omega-3 docosapentaenoic acid C22:5 n-3 (DPA), omega-6 docosapentaenoic acid C22:5 n-6 (DPA), arachidonic acid C20:4 n-6 (ARA), eicosapentaenoic acid C20:5 n-3 (EPA), stearidonic acid (SDA), linolenic acid (LLA), alpha linolenic acid (ALA), gamma linolenic acid (GLA), conjugated linolenic acid (CLA) or mixtures thereof. The PUFAs can also be present in any of the common forms found in natural lipids including but not limited to triacylglycerols, diacylglycerols, monoacylglycerols, phospholipids, free fatty acids, or in natural or synthetic derivative forms of these fatty acids (e.g. calcium salts of fatty acids, and the like). Reference to an oil or other composition comprising triglycerides having PUFA residues, as used in the present invention, can refer to either a composition comprising triglycerides having only a single type of LC PUFA residue such as DHA or a composition comprising triglycerides having a mixture of more than one type of LC PUFA residues such as more than one of DHA, EPA and ARA.

Compositions comprising triglycerides having PUFA residues can be obtained from or derived from any suitable source, such as a plant (including oilseeds), a microorganism, an animal, or mixtures of the foregoing. The microorganisms can be algae, bacteria, fungi or protists. Microbial sources and methods for growing microorganisms comprising nutrients and/or PUFAs are known in the art (Industrial Microbiology and Biotechnology, 2nd edition, 1999, American Society for Microbiology). For example, the microorganisms can be cultured in a fermentation medium in a fermentor. Oils produced by microorganisms can be used in the methods and compositions of the present invention. In some embodiments, organisms include those selected from the group consisting of golden algae (such as microorganisms of the kingdom Stramenopiles), green algae, diatoms, dinoflagellates (such as microorganisms of the order Dinophyceae including members of the genus *Crypthecodinium* such as, for example, *Crypthecodinium cohnii*), yeast, and fungi of the genera *Mucor* and *Mortierella*, including but not limited to *Mortierella alpina* and *Mortierella* sect. *schmuckeri*. Members of the microbial group Stramenopiles include microalgae and algae-like microorganisms, including the following groups of microorganisms: Hamatores, Proteromonads, Opalines, Develpayella, *Diplophrys*, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatoms, Xanthophytes, Phaeophytes (brown algae), Eustigmatophytes, Raphidophytes, Synurids, Axodines (including Rhizochromulinaales, Pedinellales, Dictyochales), Chrysomeridales, Sarcinochrysidales, Hydrurales, Hibberdiales, and Chromulinales. The Thraustochytrids include the genera *Schizochytrium* (species include *aggregatum, limnaceum, mangrovei, minutum, octosporum*), *Thraustochytrium* (species include *arudimentale, aureum, benthicola, globosum, kinnei, motivum, multirudimentale, pachydermum, proliferum, roseum, striatum*), *Ulkenia* (species include *amoeboidea, kerguelensis, minuta, profunda, radiate, sailens, sarkariana, schizochytrops, visurgensis, yorkensis*), *Aplanochytrium* (species include *haliotidis, kerguelensis, profunda, stocchinoi*), *Japonochytrium* (species include *marinum*), *Althornia* (species include *crouchii*), and *Elina* (species include *marisalba, sinorifica*). The Labrinthulids include the genera *Labyrinthula* (species include *algeriensis, coenocystis, chattonii, macrocystis, macrocystis atlantica, macrocystis macrocystis, marina, minuta, roscoffensis, valkanovii, vitellina, vitellina pacifica, vitellina vitellina, zopfi*), *Labyrinthomyxa* (species include *marina*), *Labyrinthuloides* (species include *haliotidis, yorkensis*), *Diplophrys* (species include *archeri*), *Pyrrhosorus\** (species include *marinus*), *Sorodiplophrys\** (species include *stercorea*), *Chlamydomyxa\** (species include *labyrinthuloides, montana*). (\*=there is no current general consensus on the exact taxonomic placement of these genera).

Suitable microorganisms include those capable of producing lipids comprising omega-3 and/or omega-6 polyunsaturated fatty acids, and in particular microorganisms that are capable of producing oils containing DHA, DPA, EPA or ARA will be described. More particularly, preferred microorganisms are algae, such as Thraustochytrids of the order Thraustochytriales, including *Thraustochytrium* (including *Ulkenia*) and *Schizochytrium* and including Thraustochytriales which are disclosed in commonly assigned U.S. Pat. Nos. 5,340,594 and 5,340,742, both issued to Barclay, all of which are incorporated herein by reference in their entirety. More preferably, the microorganisms are selected from the group consisting of microorganisms having the identifying characteristics of ATCC number 20888, ATCC number 20889, ATCC number 20890, ATCC number 20891 and ATCC number 20892. Since there is some disagreement among experts as to whether *Ulkenia* is a separate genus from the genus *Thraustochytrium*, for the purposes of this application, the genus *Thraustochytrium* will include *Ulkenia*. Also preferred are strains of *Mortierella schmuckeri* (e.g., including ATCC 74371) and *Mortierella alpina*. Also preferred are strains of *Crypthecodinium cohnii*, including microorganisms having the identifying characteristics of ATCC Nos. 30021, 30334-30348, 30541-30543, 30555-30557, 30571, 30572, 30772-30775, 30812, 40750, 50050-50060, and 50297-50300. Oleaginous microorganisms are also preferred. As used herein, "oleaginous microorganisms" are defined as microorganisms capable of accumulating greater than 20% of the dry weight of their cells in the form of lipids. Genetically modified microorganisms that produce PUFA-containing oils are also suitable for the present invention. These can include naturally PUFA-producing microorganisms that have been genetically modified as well as microorganisms that do not naturally produce PUFAs but that have been genetically modified to do so.

Suitable organisms can be obtained from a number of available sources, including by collection from the natural environment. For example, the American Type Culture Collection currently lists many publicly available strains of microorganisms identified above. As used herein, any organism, or any specific type of organism, includes wild strains, mutants, or recombinant types. Growth conditions in which to culture or grow these organisms are known in the art, and appropriate growth conditions for at least some of these organisms are disclosed in, for example, U.S. Pat. No. 5,130,242, U.S. Pat. No. 5,407,957, U.S. Pat. No. 5,397,591, U.S. Pat. No. 5,492,938, U.S. Pat. No. 5,711,983 and U.S. Pat. No. 6,607,900, all of which are incorporated herein by reference in their entirety. When microbial oils are used, the microorganisms are cultured in an effective medium, herein defined as any medium capable of promoting oil production. Preferably, the effective medium also promotes rapid microbial growth. The microorganisms can be cultured in conventional fermentation modes, which include, but are not limited to, batch, fed-batch, and continuous.

Another source of oils suitable for the compositions and methods of the present invention includes a plant source, such as oilseed plants. PUFA-producing plants, in alternate embodiments, can include those genetically engineered to express genes that produce PUFAs and those that produce PUFAs naturally. Such genes can include genes encoding proteins involved in the classical fatty acid synthase pathways, or genes encoding proteins involved in the PUFA polyketide synthase (PKS) pathway. The genes and proteins involved in the classical fatty acid synthase pathways, and genetically modified organisms, such as plants, transformed with such genes, are described, for example, in Napier and Sayanova, *Proceedings of the Nutrition Society* (2005), 64:387-393; Robert et al., *Functional Plant Biology* (2005) 32:473-479; or U.S. Patent Application Publication 2004/0172682. The PUFA PKS pathway, genes and proteins included in this pathway, and genetically modified microorganisms and plants transformed with such genes for the expression and production of PUFAs are described in detail in: U.S. Pat. No. 6,140,486, U.S. Pat. No. 6,566,583; U.S. Patent Application Publication No. 20020194641, U.S. Pat. No. 7,211,418, U.S. Patent Application Publication No. 20050100995A1, U.S. Patent Application Publication No. 20070089199, PCT Publication No. WO 05/097982, and U.S. Patent Application Publication No. 20050014231, each of which is incorporated herein by reference in its entirety.

Oilseed crops suitable for use in the present invention include soybeans, corn, rice, safflower, sunflower, canola, flax, peanut, mustard, rapeseed, chickpea, cotton, lentil, white clover, olive, palm oil, borage, evening primrose, linseed, and tobacco that have been genetically modified to produce a PUFA as described above.

Genetic transformation techniques for microorganisms and plants are well-known in the art. Transformation techniques for microorganisms are well known in the art and are discussed, for example, in Sambrook et al., 1989, *Molecular Cloning: A Laboratory Manual*, Cold Spring Harbor Labs Press. A general technique for transformation of dinoflagellates, which can be adapted for use with *Crypthecodinium cohnii*, is described in detail in Lohuis and Miller, *The Plant Journal* (1998) 13(3): 427-435. A general technique for genetic transformation of Thraustochytrids is described in detail in U.S. Patent Application Publication No. 20030166207, published Sep. 4, 2003. Methods for the genetic engineering of plants are also well known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119. See also, Horsch et al., *Science* 227:1229 (1985); Kado, C. I., *Crit. Rev. Plant. Sci.* 10:1 (1991); Moloney et al., *Plant Cell Reports* 8:238 (1989); U.S. Pat. No. 4,940,838; U.S. Pat. No. 5,464,763; Sanford et al., *Part. Sci. Technol.* 5:27 (1987); Sanford, J. C., *Trends Biotech.* 6:299 (1988); Sanford, J. C., *Physiol. Plant* 79:206 (1990); Klein et al., *Biotechnology* 10:268 (1992); Zhang et al., *Bio/Technology* 9:996 (1991); Deshayes et al., *EMBO J.*, 4:2731 (1985); Christou et al., *Proc Natl. Acad. Sci. USA* 84:3962 (1987); Hain et al., *Mol. Gen. Genet.* 199:161 (1985); Draper et al., *Plant Cell Physiol.* 23:451 (1982); Donn et al., In Abstracts of VIIth International Congress on Plant Cell and Tissue Culture IAPTC, A2-38, p. 53 (1990); D'Halluin et al., *Plant Cell* 4:1495-1505 (1992) and Spencer et al., *Plant Mol. Biol.* 24:51-61 (1994).

When oilseed plants are the source of PUFA-containing oils, the seeds can be harvested and processed to remove any impurities, debris or indigestible portions from the harvested seeds. Processing steps vary depending on the type of oilseed and are known in the art. Processing steps can include threshing (such as, for example, when soybean seeds are separated from the pods), dehulling (removing the dry outer covering, or husk, of a fruit, seed, or nut), drying, cleaning, grinding, milling and flaking. After the seeds have been processed to remove any impurities, debris or indigestible materials, they can be added to an aqueous solution and then mixed to produce a slurry. In some embodiments, milling, crushing or flaking is performed prior to mixing with water. A slurry produced in this manner can be treated and processed the same way as described for a microbial fermentation broth.

Another biomass source of PUFA-containing oils suitable for the compositions and methods of the present invention includes an animal source. Examples of animal sources include aquatic animals (e.g., fish, marine mammals, and crustaceans such as krill and other euphausids) and animal tissues (e.g., brain, liver, eyes, etc.) and animal products such as eggs or milk. Techniques for recovery of PUFA-containing oils from such sources are known in the art.

While in one embodiment of the invention the composition comprising triglycerides having PUFA residues can be a crude oil (discussed in more detail below), other such compositions useful in the present invention can be recovered from their sources by any suitable means known to those in the art. For example, oils can be recovered by extraction with solvents such as chloroform, hexane, methylene chloride, methanol and the like, or by supercritical fluid extraction. Alternatively, the oils can be extracted using extraction techniques, such as are described in U.S. Pat. No. 6,750,048 and PCT Patent Application Ser. No. 01/01806, both filed Jan. 19, 2001, and entitled "Solventless Extraction Process," both of which are incorporated herein by reference in their entirety. Additional extraction and/or purification techniques are taught in PCT Patent Application Serial No. PCT/IB01/00841 entitled "Method for the Fractionation of Oil and Polar Lipid-Containing Native Raw Materials" filed Apr. 12, 2001; PCT Patent Application Serial No. PCT/IB01/00963 entitled "Method for the Fractionation of Oil and Polar Lipid-Containing Native Raw Materials Using Water-Soluble Organic Solvent and Centrifugation" filed Apr. 12, 2001; U.S. Provisional Patent Application Ser. No.

60/291,484 entitled "Production and Use of a Polar Lipid-Rich Fraction Containing Stearidonic Acid and Gamma Linolenic Acid from Plant Seeds and Microbes filed May 14, 2001; U.S. Provisional Patent Application Ser. No. 60/290,899 entitled "Production and Use of a Polar-Lipid Fraction Containing Omega-3 and/or Omega-6 Highly Unsaturated Fatty Acids from Microbes, Genetically Modified Plant Seeds and Marine Organisms" filed May 14, 2001; U.S. Pat. No. 6,399,803 entitled "Process for Separating a Triglyceride Comprising a Docosahexaenoic Acid Residue from a Mixture of Triglycerides" issued Jun. 4, 2002 filed Feb. 17, 2000; and PCT Patent Application Ser. No. 01/01010 entitled "Process for Making an Enriched Mixture of Polyunsaturated Fatty Acid Esters" filed Jan. 11, 2001; all of which are incorporated herein by reference in their entirety. The extracted oils can be evaporated under reduced pressure to produce a sample of concentrated oil material. Processes for the enzyme treatment of biomass for the recovery of lipids are disclosed in U.S. Provisional Patent Application No. 60/377,550, entitled "HIGH-QUALITY LIPIDS AND METHODS FOR PRODUCING BY ENZYMATIC LIBERATION FROM BIOMASS," filed on May 3, 2002; PCT Patent Application Serial No. PCT/US03/14177 entitled "HIGH-QUALITY LIPIDS AND METHODS FOR PRODUCING BY ENZYMATIC LIBERATION FROM BIOMASS," filed on May 5, 2003; copending U.S. patent application Ser. No. 10/971,723, entitled "HIGH-QUALITY LIPIDS AND METHODS FOR PRODUCING BY LIBERATION FROM BIOMASS," filed on Oct. 22, 2004; EP Patent Publication 0 776 356 and U.S. Pat. No. 5,928,696, both entitled "Process for extracting native products which are not water-soluble from native substance mixtures by centrifugal force," the disclosures of which are hereby incorporated by reference herein in their entirety.

In some embodiments, an oil obtained from a source described above can serve as the starting material for the methods of the present invention even when it has not been subjected to conventional processing. Examples of such conventional processes that may be avoided include refining (e.g., physical refining, silica refining or caustic refining), desolventization, deodorization, winterization, chill filtration, and/or bleaching. Thus, in certain embodiments, the composition containing triglycerides having PUFA residues has not been subjected to one or more treatments selected from refining, desolventization, deodorization, winterization, chill filtration, and bleaching and in further embodiments, the composition has not been subjected to any one of refining, desolventization, deodorization, winterization, chill filtration, and bleaching.

In further aspects of the invention, the composition comprising triglycerides having polyunsaturated fatty acid residues may be an oil having characteristics of oils that have not been subjected to conventional processing, such as refining, desolventization, deodorization, winterization, chill filtration, and bleaching. Thus, a suitable oil can have a chemical or physical characteristic of an unprocessed oil. For example, the oil may contain an undesirable component (e.g., an impurity) at a level that is typically not present in a conventionally processed oil. For example, the oil may contain from about 300 ppm phosphorous to about 1000 ppm phosphorous. In some embodiments, the oil comprises at least about 300 ppm phosphorous; at least about 400 ppm phosphorous; at least about 500 ppm phosphorous; at least about 600 ppm phosphorous; at least about 650 ppm phosphorous; at least about 700 ppm phosphorous; at least about 750 ppm phosphorous; at least about 800 ppm phosphorous; at least about 850 ppm phosphorous; at least about 900 ppm phosphorous; at least about 950 ppm phosphorous; or at least about 1000 ppm phosphorous. In another aspect, the oil may contain free fatty acids in a range of from about 0.4 wt. % to about 1.4 wt. %. In certain embodiments, the oil comprises at least about 0.4 wt. % free fatty acids; at least about 0.6 wt. % free fatty acids; at least about 0.8 wt. % free fatty acids; at least about 0.9 wt. % free fatty acids; at least about 1.0 wt. % free fatty acids; at least about 1.1 wt. % free fatty acids; at least about 1.2 wt. % free fatty acids; at least about 1.3 wt. % free fatty acids; or at least about 1.4 wt. % free fatty acids. In another aspect, the oil may contain a peroxide value ranging from about 0.2 meq/kg to about 2.5 meq/kg. In some embodiments, the oil comprises a peroxide value of at least about 0.2 meq/kg; a peroxide value of at least about 0.4 meq/kg; a peroxide value of at least about 0.6 meq/kg; a peroxide value of at least about 0.8 meq/kg; a peroxide value of at least about 1.0 meq/kg; a peroxide value of at least about 1.2 meq/kg; a peroxide value of at least about 1.4 meq/kg; a peroxide value of at least about 1.5 meq/kg; a peroxide value of at least about 1.6 meq/kg; a peroxide value of at least about 1.7 meq/kg; a peroxide value of at least about 1.8 meq/kg; a peroxide value of at least about 1.9 meq/kg; a peroxide value of at least about 2.0 meq/kg; a peroxide value of at least about 2.1 meq/kg; a peroxide value of at least about 2.2 meq/kg; a peroxide value of at least about 2.3 meq/kg; a peroxide value of at least about 2.4 meq/kg; or a peroxide value of at least about 2.5 meq/kg.

In some embodiments, the crude oil may be isolated from a microorganism using standard techniques, without being subjected to further refinement or purification. In such embodiments, the oil is a microbial oil that has only been subjected to solvent extraction, such as hexane extraction, isopropanol extraction, or the like.

In other embodiments, compositions comprising triglycerides having polyunsaturated fatty acid residues, such as oils described above, may be subjected to further processing steps, such as refining, desolventization, deodorization, winterization, chill filtration, and/or bleaching. Such "processed" oils include microbial oils that have been subjected to solvent extraction and one or more of these additional processing steps. In some embodiments, oils are minimally processed. "Minimally processed" oils include microbial oils that have been subjected to solvent extraction and filtration. In certain embodiments, minimally processed oils are further subjected to winterization.

Methods of the present invention involve reacting compositions containing triglycerides having PUFA residues in the presence of an alcohol and a base to produce esters of the PUFAs from the triglycerides.

Alcohols suitable for use in the present invention include any lower alkyl alcohol containing from 1 to 6 carbon atoms (i.e., a $C_{1-6}$ alkyl alcohol). Without being bound by theory, it is believed that the use of lower alkyl alcohols in the methods of the present invention produces lower alkyl esters of the PUFAs. For example, the use of ethanol produces ethyl esters. In certain embodiments, the alcohol is methanol or ethanol. In these embodiments, the PUFA esters produced are a methyl ester and an ethyl ester of the PUFA, respectively. In processes of the present invention, the alcohol typically comprises between about 25 wt. % and about 50 wt. %; between about 30 wt. % and about 45 wt. %, or between about 35 wt. % and about 40 wt. % of the mixture of the composition, the alcohol and the base. In some embodiments, the alcohol comprises about 38 wt. % of the mixture of the composition, the alcohol and the base. In certain embodiments, the composition and the base can be added to either pure ethanol or pure methanol. In general, the amount of alcohol used may vary with the solubility of the oil or composition containing triglycerides having PUFA residues in the alcohol.

Any base known in the art to be suitable for use as a reactant may be used in the present invention. Bases of the formula RO-M, wherein M is a monovalent cation and RO is an alkoxide of a $C_{1-6}$ alkyl alcohol are particularly suited for the present invention. Examples of suitable bases include elemental sodium, sodium methoxide, sodium ethoxide, potassium methoxide, and potassium ethoxide. In some embodiments, the base is sodium ethoxide. In processes of the present invention, the base is typically added in an amount of between about 0.5 and about 1.5 molar equivalents of triglycerides, between about 0.7 and about 1.4 molar equivalents of triglycerides, between about 0.9 and about 1.3 molar equivalents of triglycerides, or between about 1.0 and about 1.2 molar equivalents of triglycerides to the reaction step with the composition and the alcohol. In certain embodiments, the base is typically added in an amount of about 0.1, 0.2, 0.3, 0.4, 0.5, 0.6, 0.7, 0.8, 0.9, 0.95, 1.0, 1.01, 1.02, 1.03, 1.04, 1.05, 1.10, 1.15, 1.2, 1.3, 1.4, or 1.5 molar equivalents of triglycerides to the reaction step with the composition and the alcohol. In some embodiments, the base is added in an amount of 1.04 molar equivalents of triglycerides to the reaction step with the composition and the alcohol.

The composition comprising triglycerides having polyunsaturated fatty acid residues, the alcohol and the base are reacted together at a temperature and for an amount of time that allows the production of an ester between the fatty acid residues and the alcohol. Suitable reaction times and temperatures may be determined by one of skill in the art to produce an ester. Without intending to be bound by theory, the PUFA residues are believed to be cleaved from the glycerol backbone of the triglyceride and esters of each PUFA residue are formed during the step of reacting. In certain embodiments, the step of reacting the composition in the presence of an alcohol and a base is performed at a temperature from about 60° C. to about 120° C., from about 70° C. to about 110° C., from about 75° C. to about 100° C., or from about 80° C. to about 90° C. In further embodiments, the step of reacting the composition in the presence of an alcohol and a base is performed at a temperature of about 75° C., 80° C., 85° C., 90° C., or 95° C. In some embodiments, the step of reacting the composition in the presence of an alcohol and a base is performed for a time from about 2 hours to about 12 hours, from about 3 hours to about 11 hours, from about 4 hours to about 10 hours, from about 5 hours to about 9 hours, or from about 6 hours to about 8 hours. In certain embodiments, the step of reacting the composition in the presence of an alcohol and a base is performed for about 5.5, 6, 6.5, 7, 7.5, 8, or 8.5 hours In one embodiment, the step of reacting the oil composition, alcohol and base may be conducted by refluxing the components to produce the PUFA esters. In additional embodiments, the step of reacting the oil composition may be carried out at a temperature that does not result in the refluxing of the reaction components. For example, carrying out the step of reacting the oil composition under pressures greater than atmospheric pressure can increase the boiling point of the solvents present in the reaction mixture. Under such conditions, the reaction can occur at a temperature at which the solvents would boil at atmospheric pressure, but would not result in the refluxing of the reaction components. In some embodiments, the reaction is conducted at a pressure from about 5 to about 20 pounds per square inch (psi); from about 7 to about 15 psi; or from about 9 to about 12 psi.

In certain embodiments, the reaction is conducted at a pressure of about 7, 8, 9, 10, 11, or 12 psi. Reactions conducted under pressure may be carried out at the reaction temperatures listed above. In some embodiments, reactions conducted under pressure may be carried out at about 70° C., 75° C., 80° C., 85° C., or 90° C.

The reaction mixture comprising PUFA esters can be further processed to obtain the PUFA esters from the mixture. For example, the mixture may be cooled, diluted with water, and the aqueous solution extracted with a solvent such as hexane to produce a composition comprising PUFA esters. Techniques for washing and/or extracting crude reaction mixtures are known in the art.

In one embodiment of the present invention, PUFA esters are separated from the reaction mixture by distilling the composition to recover a fraction comprising the ester of the polyunsaturated fatty acid. In this manner, a targeted fraction of the reaction mixture including PUFA esters of interest can be separated from the reaction mixture and recovered.

In certain embodiments, the distillation is performed under vacuum. Without being bound by theory, distillation under vacuum allows the distillation to be accomplished at a lower temperature than in the absence of a vacuum and thus may prevent the degradation of the esters. Typical distillation temperatures range from about 120° C. to about 170° C. In some embodiments, the step of distilling is performed at a temperature of less than about 180° C., less than about 175° C., less than about 170° C., less than about 165° C., less than about 160° C., less than about 155° C., less than about 150° C., less than about 145° C., less than about 140° C., less than about 135° C., or less than about 130° C. Typical pressures for vacuum distillation range from about 0.1 mm Hg to about 10 mm Hg. In some embodiments, the pressure for vacuum distillation is about 0.1, 0.5, 1, 1.5, 2, 2, 5, 3, 3.5, or 4 mm Hg.

The methods of the present invention may be used to produce compositions that contain a high percentage of PUFA esters. For example, such compositions can contain between about 50 wt. % and about 100 wt. % of an ester of a PUFA, and in other embodiments, the composition can comprise at least about 50 wt. %, at least about 55 wt. %, at least about 60 wt. %, at least about 65 wt. %, at least about 70 wt. %, at least about 75 wt. %, at least about 80 wt. %, at least about 85 wt. %, at least about 90 wt. %, at least about 95 wt. %, at least about 99 wt. % of esters of a PUFA.

In some embodiments, the PUFA esters are subjected to a urea crystallization step. When urea crystallizes in a solution containing PUFA esters (e.g., esters of DHA) and saturated fatty acid esters formed by the transesterification of a glyceride source using the techniques discussed above, a precipitate forms that comprises the urea and at least a portion of the saturated fatty acid esters. This precipitate, however, comprises a substantially lesser fraction of the PUFA esters than the initial reaction mixture. The bulk of the PUFA esters instead remain in solution and can therefore be easily separated from the precipitated saturated fatty acid esters.

The urea crystallization separation process comprises first forming a solution comprising fatty acid esters and urea. The amount of urea preferably is proportional to the total amount of saturated fatty acids to be separated from the solution. When separating fatty acid esters from the transesterification reaction mixtures described above, the mass ratio of the mixture of fatty acid esters to urea is typically about 1:2. The solution also preferably comprises an organic solvent that can solubilize urea and the desired PUFA ester, and more preferably can solubilize urea and all the fatty acid esters in the mixture. Examples of suitable solvents include alkyl alcohols having from 1 to 4 carbons, with methanol and ethanol being more preferred, and ethanol being the most preferred. The volumetric ratio of the mixture of fatty acid esters to solvent is preferably about 1:10.

Essentially all the urea preferably is dissolved in the solution. This may generally be achieved by heating the solution. The solution, however, preferably is not heated to a temperature above the boiling point of the organic solvent. Typically, the solution is heated to a temperature of about 60° C., 65° C., 70° C., 75° C. or 80° C.

Once the urea is dissolved, the PUFA esters are added to the solution. Upon addition, if solids remain, the mixture may be heated until solids dissolve. The solution may be cooled to form a precipitate comprising urea adducts of fatty acid esters. In certain embodiments, the solution is cooled to a temperature that is from about 0° C. to about 25° C., such as from about 15° C. to about 25° C. In other embodiments, the solution is cooled to a temperature of about 0° C. about 5° C. about 10° C. about 15° C., about 20° C., about 25° C., or from about 20° C. to about 25° C. Once the solution is cooled, it may be allowed to stand for a period of time (typically no greater than about 20 hours) at the cooling temperature with occasional stirring.

In another embodiment of this invention, after the solution (comprising fatty acid esters and dissolved urea) is formed, a precipitate comprising urea is formed by concentrating the solution. The solution may be concentrated, for example, by evaporating a portion of the solvent in the solution. The amount of solvent removed preferably is sufficient to cause the urea concentration in the solution to exceed the saturation concentration.

During the urea crystallization separation process, the solution may be kept in a non-oxidizing atmosphere, such as an atmosphere consisting essentially of a noble gas, $N_2$, or a combination thereof, with an atmosphere consisting essentially of $N_2$ being most preferred. Use of such an atmosphere may aid in minimizing oxidation of carbon-carbon double bonds of the PUFA esters.

After the precipitate comprising urea has formed, the precipitate may be separated from the liquid fraction enriched in PUFA esters. This may be achieved, for example, by filtration or centrifugation. In one embodiment, the precipitate may be subsequently washed with a small quantity of the organic solvent (preferably saturated with urea) to recover any residual unprecipitated desired PUFA ester that remains with the precipitate. This solvent, in turn, may be combined with the liquid fraction.

The liquid fraction may be concentrated, combined with water, and then the esters therein may be extracted with a non-polar solvent from the resulting mixture. The liquid fraction may be concentrated, for example, by evaporating a portion of the solvent from the liquid fraction (the amount of solvent evaporated, however, preferably is not so great as to cause further urea to precipitate). The amount of water subsequently combined with the resulting concentrated liquid fraction may vary widely. Preferably, the volume ratio of water to concentrated liquid fraction is about 2:1 (in a particularly preferred embodiment, sufficient acid (preferably $H_2SO_4$) is also introduced to neutralize the urea). The non-polar solvent that may be used to extract the fatty acid esters from the resulting concentrated-mother-liquor/water mixture may be, for example, petroleum ether, pentane, hexane, cyclohexane, ethyl acetate, or heptane, with hexane being the most preferred. The volumetric ratio of the non-polar solvent to the concentrated-mother-liquor/water mixture preferably is about 2:3.

In other embodiments, the liquid fraction may also be extracted with a slightly polar organic solvent to maximize recovery of the fatty acid esters (which are slightly polar). Examples of suitable slightly polar solvents include diethyl ether and ethyl acetate, with diethyl ether being most preferred. Preferably, the volumetric ratio of slightly polar solvent to the mother-liquor/water mixture is about 2:3. Following the extraction with this slightly polar solvent, the solvent preferably may be combined with the non-polar solvent used in the initial extraction.

After the extraction is complete, any residual water may be removed from the extraction solvent by, for example, washing the solvent with brine and/or passing the solvent over an anhydrous salt (e.g., sodium sulfate). The solution then preferably is concentrated by, for example, evaporating a portion of the solvent.

By way of example, the methods of the present invention may be used to purify ethyl arachidonate (arachidonic acid ethyl ester) from a crude *Mortierella alpina* oil. A crude oil obtained from *Mortierella alpina* by hexane extraction (typically with an ARA content of about 0.5 g/g oil) can be used directly without any further processing, such as winterization and/or RBD processing. 150 mL of absolute ethanol can be added to 175 g (approximately 0.2 moles) of the crude oil in a one-liter flask under $N_2$ at room temperature. The mixture can be allowed to stir for 15 minutes to obtain a homogeneous solution. 67 g of a 21% solution of NaOEt/EtOH (approximately 1.04 molar equivalents) can be then added to the solution, and the mixture can be allowed to reflux under $N_2$ for about 10 hours. The progress of the reaction may be monitored by gas chromatography (GC) and/or thin-layer chromatography (TLC).

When the reaction is completed, approximately 75 mL of ethanol can be removed by distillation, and the mixture can be allowed to cool to room temperature under $N_2$. 300 mL of hexane can be added to the cooled mixture, and the mixture can be allowed to stir for 15 minutes at room temperature. 300 mL of deionized water can be then added to the mixture, and the mixture can be allowed to stir for an additional 15 minutes. After removing and saving the organic layer, the aqueous layer can be washed twice with 300 mL portions of hexane. The combined organic layer can be washed with 200 mL of a saturated NaCl solution. A GC analysis of the organic layer may be used to determine the amount of ARA ethyl ester present in the crude product. In some embodiments, approximately 50% of the crude product is ARA ethyl ester, with the remaining materials being predominantly lower molecular weight ethyl esters. The crude product may then be subjected to vacuum fractional distillation or other purification procedures. In certain embodiments, a purity of greater than about 60% ARA ethyl ester may be achieved following the fractional distillation of the crude product.

Without being bound by theory, it is believed that the methods of the present invention result in the direct transesterification of triglycerides having PUFA residues to produce esters of the PUFAs. Previous methods utilized long reaction times, large amounts of reagents, and subjected the oils to harsh conditions such as high temperatures and highly acidic conditions. The methods disclosed herein thus provide a more efficient and economical purification process that yields a pure product. Furthermore, the methods disclosed herein may be applied to crude oils as well as purified oils, resulting in an additional increase in efficiency and cost savings.

Other embodiments of the present invention include compositions produced by the methods described herein. As noted above, such compositions can contain greater than about 50 wt. %, greater than about 55 wt. %, etc. of esters of a PUFA. In such embodiments, the compositions can contain at least about 89, 90, 91, 92, 93, 94, 95, 96, 97, 98, or 99 wt. % of PUFA esters. In other embodiments, the compositions may further comprise less than about 10, 9, 8, 7, 6, 5, 4, 3, 2, 1, 0.5, 0.25 or 0.1 wt. % eicosapentaenoic acid. The compositions of the invention may include any PUFA esters as described above, namely, DHA, omega-3 DPA, omega-6 DPA, ARA, SDA, LLA, ALA, GLA, or CLA or combinations thereof. In some embodiments, the compositions may comprise ethyl esters. In certain embodiments, the composition comprises at least about 89 wt. % DHA esters. In other embodiments, the composition comprises at least about 89 wt. % of a combination of DHA and DPA esters.

Compositions of the present invention also include compositions that contain at least about 60, 65, 70, 75, 80, 85, 90, or 95 wt. % ARA esters. In some embodiments, the ARA esters may be ethyl esters of ARA. In other embodiments, the compositions may further comprise less than about 10, 9, 8, 7, 6, 5, 4, 3, 2, 1, 0.5, 0.25 or 0.1 wt. % eicosapentaenoic acid.

The present invention also provides compositions comprising at least about 90 wt. % ethyl ester of docosahexaenoic acid (DHA) and at least about 0.1 wt. % of 4, 7, 10, 13, 16, 19, 22, 25 octacosaoctaenoic acid (C28:8). These compositions may be produced by the methods disclosed herein. In some embodiments, the amount of ethyl ester of DHA in the compositions may be at least about 91, 92, 93, 94, 95, 96, 97, 98, or 99 wt. %. In certain embodiments, the amount of C28:8 in the compositions may be at least about 0.2, 0.3, 0.4, 0.5, 0.6, 0.7, 0.8, 0.9, 1.0, 1.1, 1.2, 1.3, 1.4 or 1.5 wt. %. The C28:8 may be present in triglyceride or ester form. For example, the C28:8 may be present in ethyl ester form.

The present invention also provides compositions comprising at least about 90 wt. % ethyl ester of docosahexaenoic acid (DHA) and at least about 0.1 wt % of DPA (n-3). These compositions may be produced by the methods disclosed herein. In some embodiments, the amount of ethyl ester of DHA in the compositions may be at least about 91, 92, 93, 94, 95, 96, 97, 98, or 99 wt. %. In certain embodiments, the amount of DPA (n-3) in the compositions may be at least about 0.1, 0.2, 0.3, 0.4, 0.5, 0.6, 0.7, 0.8, 0.9, or 1.0 wt. % of DPA (n-3). The DPA (n-3) may be present in triglyceride or ester form. For example, the DPA (n-3) may be present in ethyl ester form.

In certain embodiments, the compositions comprise all three of the ethyl ester of DHA, C28:8 and DPA (n-3) in the concentration ranges specified above.

In further embodiments, the compositions may comprise less than about 1.0, 0.9, 0.8. 0.7, 0.6, 0.5, 0.4, 0.3, 0.2, or 0.1 wt. % EPA in addition to the ethyl ester of DHA and C28:8. In one embodiment, the compositions may comprise less than about 0.25 wt. % EPA. The EPA may be present in triglyceride or ester form. For example, the EPA may be present in ethyl ester form. In some embodiments, the compositions may comprise 0 wt. % EPA.

The present invention also provides compositions comprising at least about 90 wt. % ethyl ester of docosahexaenoic acid and at least one additional fatty acid or an ester thereof. In some embodiments, the amount of ethyl ester of DHA in the compositions may be at least about 91, 92, 93, 94, 95, 96, 97, 98, or 99 wt. %. In certain embodiments, the additional fatty acid may have a boiling point of about 150-170° C. at a pressure of 0.8 mm Hg.

The present invention further includes compositions comprising at least about 70 wt. % ethyl ester of docosahexaenoic acid (DHA) and at least about 25 wt. % ethyl ester of docosapentaenoic acid (n-6).

Compositions of the present invention also include compositions that comprises at least about 90 wt. % of a combination of ethyl ester of docosahexaenoic acid and ethyl ester of docosapentaenoic acid (n-6). In certain embodiments, the compositions may comprise at least about 91, 92, 93, 94, 95, 96, 97, 98, or 99 wt. % of a combination of ethyl ester of docosahexaenoic acid and ethyl ester of docosapentaenoic acid (n-6). In some embodiments, the compositions may comprise at least about 10 wt. % ethyl ester of docosahexaenoic acid and at least about 10 wt. % ethyl ester of docosapentaenoic acid (n-6). In other embodiments, the compositions may comprise at least about 15 or 20 wt. % ethyl ester of docosahexaenoic acid and at least about 15 or 20 wt. % ethyl ester of docosapentaenoic acid (n-6).

The present invention also provides compositions comprising at least about 90 wt. % of a combination of ethyl ester of docosahexaenoic acid and ethyl ester of docosapentaenoic acid (n-6), and at least one additional fatty acid or an ester thereof. In certain embodiments, the compositions may comprise at least about 91, 92, 93, 94, 95, 96, 97, 98, or 99 wt. % of a combination of ethyl ester of docosahexaenoic acid and ethyl ester of docosapentaenoic acid (n-6). In some embodiments, the additional fatty acid may have a boiling point of about 150-170° C. at a pressure of 0.8 mm Hg.

The DHA/DPA (n-6) compositions described above may further comprise less than about 4% of a saturated fatty acid or an ester thereof. In certain embodiments, the compositions may comprise less than about 3.5%, 3.0%, 2.5%, 2.0%, 1.5%, 1.0% or 0.5% of a saturated fatty acid or an ester thereof.

In some embodiments, the saturated fatty acid or an ester thereof may contain less than 20 carbons, such as, for example, a saturated fatty acid or an ester thereof that contains 19, 18, 17. 16, 15, 14, 13, 12, 11, 10, 9 or 8 carbons. In certain embodiments, the saturated fatty acid or ester thereof may contain 14 or 16 carbons.

PUFA esters and compositions of the present invention (at times referred to collectively as "PUFA esters") may be used in pharmaceutical products. In some embodiments, the pharmaceutical products may contain PUFA esters without an additional pharmaceutically active agent. In other embodiments, the pharmaceutical product may comprise a pharmaceutically active agent. Examples of pharmaceutically active agents include statins, anti-hypertensive agents, anti-diabetic agents, anti-dementia agents, anti-depressants, anti-obesity agents, appetite suppressants and agents to enhance memory and/or cognitive function. The pharmaceutical products may further comprises any pharmaceutically acceptable excipient, carriers, binders or other formulation components known in the art.

PUFA esters produced by the methods of the present invention and compositions of the present invention are suitable for use as therapeutic and experimental agents. An embodiment of the present invention comprises the production of PUFA esters for treatment of PUFA-deficient infants. The PUFA esters can be included in a parenteral formulation that can be administered to an infant through parenteral routes to fortify the infant's supply of a PUFA. Preferred parenteral routes include, but are not limited to, subcutaneous, intradermal, intravenous, intramuscular and intraperitoneal routes. A parenteral formulation can include PUFA esters of the present invention and a carrier suitable for parenteral delivery. As used herein, a "carrier" refers to any substance suitable as a vehicle for delivering a molecule or composition to a suitable in vivo site of action. Examples of such carriers include, but are not limited to water, phosphate buffered saline, Ringer's solution, dextrose solution, serum-containing solutions, Hank's solution and other aqueous physiologically balanced solutions. Suitable carriers also include oil-based carriers, non-aqueous solutions, suspensions, and emulsions. Examples include propylene glycol, polyethylene glycol, vegetable oils such as olive oil, injectable organic esters such as ethyl oleate, polyethoxylated castor oil (cremaphor), and others known in the art. Acceptable protocols to administer PUFA esters in an effective manner include individual dose size, number of doses, frequency of dose administration, and mode of administration. Determination of such protocols can be accomplished by those skilled in the art depending upon a variety of variables, including the weight of the infant and the extent of PUFA deficiency. Another embodiment of the present invention comprises the production of PUFA esters for treatment of adults, in particular pregnant mothers. The product may be used for augmenting long chain PUFA levels in milk of warm-blooded animals. Acceptable protocols for administration of PUFA esters to adults includes parenteral feeding techniques or encapsulating PUFA esters of the present invention in a capsule, such as gelatin (i.e., digestible) capsule, for oral administration and/or in a liquid diet formulation. A liquid diet formulation can comprise a liquid composition containing nutrients suitable for supplementing a diet or nutrients sufficient as a complete diet.

PUFA esters produced by the methods of the present invention and compositions of the present invention may also be used to treat subjects (e.g., humans or animals) with high levels of triglycerides, including subjects with triglyceridemia. For example, subjects with fasting triglycerides of 150 mg/dL or above may benefit from treatment with the PUFA esters of the present invention, and, additionally, the elevation of post-parandial triglyercides may be reduced by treatment with the PUFA esters of the present invention. In some embodiments, individual PUFA esters may be administered to a subject to treat high levels of triglycerides. In certain embodiments, the PUFA ester may be DHA or ARA. In other embodiments combinations of PUFA esters may be administered to a subject to treat high levels of triglycerides. In certain embodiments, the combination of PUFA esters may comprise omega-3 and omega-6 PUFAS such as DHA and DPA n-6. In some embodiments, the PUFA esters may comprise about 90% of a composition administered to the subject. The PUFA esters may be administered with other components and excipients, such as the carriers described above. The PUFA esters may also be used to treat subjects with diseases that can be associated with high levels of triglycerides, such as cardiovascular disease or hypertension.

PUFA esters and compositions of the present invention may be used to treat subjects with neurological disorders, dementia and pre-dementia related conditions. These conditions include Alzheimer's Disease, Vascular Dementia, Mixed Dementia, Dementia with Lewy Bodies, as well as secondary dementias caused by drugs, delirium, or depression.

Therapeutic compounds appropriate to use with the PUFA esters and compositions of the present invention include any therapeutic which can be used to protect an individual against any of the conditions or diseases discussed herein, and may include a protein, an amino acid, a drug, other natural products and a carbohydrate. Such therapeutic compounds will be well known to those of skill in the art for the particular disease or condition being treated. Some preferred therapeutic compounds to combine with a composition or formulation of the invention include, but are not limited to: Tacrine (COGNEX); Donepezil (ARICEPT); Rivastigmine (EXELON); Galantamine (REMINYL); Memantine (AKATINOL); Neotropin; Nootropics; Alpha-tocopherol (vitamin E); Selegeline (ELDEPRYL); non-steroidal anti-inflammatory agents (NSAIDS); Gingko biloba; estrogen; β-secretase inhibitors; vaccines, including lipid or liposome-based vaccines, that dissolve plaques in the brain; B complex vitamins; calcium channel blockers; HMG CoA reductase inhibitors; statins and other anti-cholesterol drugs (e.g., ZOCOR (simvastatin), LIPITOR (atorvastatin calcium), LESCOL (fluvastatin). LOPID (gemfibrozil), or PRAVACHOL (pravastatin sodium)); policosanols; fibrates; Clioquinol; (and other natural products (e.g., curcumin, lignans, phytoestrogens, phytosterols; niacin, and vitamin supplements).

Dosages and routes of administration are known in the art and may be determined by those of skill in the art.

Although PUFA esters and compositions of the present invention can be administered topically or as an injectable, the most preferred route of administration is oral administration. The PUFAs may be administered to individuals in the form of nutritional supplements and/or foods and/or pharmaceutical formulations and/or beverages. A preferred type of food is a medical food (e.g., a food which is in a formulation to be consumed or administered externally under the supervision of a physician and which is intended for the specific dietary management of a disease or condition for which distinctive nutritional requirements, based on recognized scientific principles, are established by medical evaluation.) For infants, the fatty acids are administered to infants as infant formula, weaning foods, jarred baby foods, human milk fortifier and/or infant cereals.

Any biologically acceptable dosage forms, and combinations thereof, are contemplated by the inventive subject matter. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables, infusions, health bars, confections, cereals, cereal coatings, foods, nutritive foods, functional foods and combinations thereof. The preparations of the above dosage forms are well known to persons of ordinary skill in the art. Preferably, a food that is enriched with the desired PUFA is selected from the group including, but not limited to: baked goods and mixes; chewing gum; breakfast cereals; cheese products; nuts and nut-based products; gelatins, pudding, and fillings; frozen dairy products; milk products; dairy product analogs; soft candy; soups and soup mixes; snack foods; processed fruit juice; processed vegetable juice; fats and oils; fish products; plant protein products; poultry products; and meat products.

The present invention also includes a method of making any of the above-described compositions of the invention, such as by combining the components of the composition into any suitable delivery form using any suitable method known in the art.

According to the present invention, the methods of the present invention are suitable for use in an individual that is a member of the Vertebrate class, Mammalia, including, without limitation, primates, livestock and domestic pets (e.g., a companion animal). Most typically, an individual will be a human individual. The term "individual" can be interchanged with the term "subject" or "patient" and refers to the subject of a protocol or method according to the invention. Accordingly, an individual can include a healthy, normal (non-diseased) individual, as well as an individual who has or is at risk of developing pre-dementia or dementia or a symptom or indicator thereof as described herein.

The PUFA esters produced by the methods of the present invention may be used to produce PUFA salts. In some embodiments, PUFA salts can be produced by reacting the PUFA esters of the present invention in the presence of an alkaline metal base such as an alkaline metal hydroxide (e.g., potassium hydroxide). The PUFA salts formed from the PUFA esters of the present invention can be used in a variety of applications, such as in foods, beverages, and pharmaceuticals. In some embodiments, the PUFA salts produced using the PUFA esters of the present invention are water-soluble and can be used directly in foods, beverages, and pharmaceuticals.

PUFA esters produced by the methods of the present invention can be used in any animal food material, particularly food materials for humans, to create a food product having enhanced concentrations of PUFAs. The amount of fatty acids naturally in food products varies from one food product to another. A food product of the present invention can have a normal amount of a PUFA or a modified amount of a PUFA. In the former instance, a portion of the naturally occurring lipids may be substituted by PUFA esters of the present invention. In the latter instance, naturally occurring lipids may be supplemented by PUFA esters of the present invention.

PUFA esters may be added to foods for infants, such as infant formula and baby food. According to the present invention, an infant refers to infants and children less than about two years old, including, in particular, premature infants. Certain PUFAs are particularly important component of infant formula and baby food because of the rapid growth of infants (i.e., doubling or tripling in weight during the first year of life). An effective amount of PUFA ester to supplement infant formula is an amount that approximates the concentration of the PUFAs in human breast milk. Preferred amounts of PUFA esters to add to infant formula or baby food range from between about 0.1 to about 1.0% of total fatty acids, more preferably from between about 0.1 to about 0.6% of total fatty acids, and even more preferably about 0.4% of total fatty acids.

Another aspect of the present invention includes a food product comprising a food material combined with PUFA esters of the present invention. PUFA esters may be added to a food material to create a food product having enhanced concentrations of PUFAs. As used herein, the term "food material" refers to any food type fed to humans or non-human animals. Also within the scope of the present invention is a method to make a food product comprising adding PUFA esters produced by methods of the present invention to a food material.

A suitable food material useful for the formation of a food product of the present invention includes animal food. The term "animal" means any organism belonging to the kingdom Animalia and includes, without limitation, primates (e.g., humans and monkeys), livestock and domestic pets. The term "food product" includes any product to be fed to such animals. Preferred food materials to be consumed by humans include infant formula and baby food. Preferred food materials to be consumed by domestic pets include dog foods.

PUFA esters produced by methods of the present invention can be added to a wide range of products such as baked goods, vitamin supplements, diet supplements, powdered drinks, etc. at various stages of production. Numerous finished or semi-finished powdered food products can be produced using the compositions of the present invention.

A partial list of food products comprising the products of the present invention includes doughs, batters, baked food items including, for example, such items as cakes, cheesecakes, pies, cupcakes, cookies, bars, breads, rolls, biscuits, muffins, pastries, scones, and croutons; liquid food products, for example, beverages, energy drinks, infant formula, liquid meals, fruit juices, multivitamin syrups, meal replacers, medicinal foods, and syrups; semi-solid food products such as baby food, yogurt, cheese, cereal, pancake mixes; food bars including energy bars; processed meats; ice creams; frozen desserts; frozen yogurts; waffle mixes; salad dressings; and replacement egg mixes. Also included are baked goods such as cookies, crackers, sweet goods, snack cakes, pies, granola/snack bars, and toaster pastries; salted snacks such as potato chips, corn chips, tortilla chips, extruded snacks, popcorn, pretzels, potato crisps, and nuts; specialty snacks such as dips, dried fruit snacks, meat snacks, pork rinds, health food bars and rice/corn cakes; and confectionary snacks such as candy.

The present invention, while disclosed in terms of specific methods, products, and organisms, is intended to include all such methods, products, and organisms obtainable and useful according to the teachings disclosed herein, including all such substitutions, modifications, and optimizations as would be available to those of ordinary skill in the art. The following examples and test results are provided for the purposes of illustration and are not intended to limit the scope of the invention.

EXAMPLES

Example 1

This example illustrates a method of the present invention for purifying ethyl docosahexaneoate (DHA ethyl ester) from docosahexaneoic acid-containing single cell oil.

150 mL of absolute ethanol (EtOH) was added to 175 g (approximately 0.2 moles of triglyceride) of DHASCO®-T oil (Martek Biosciences Corporation, Columbia, Md., having a DHA content of 0.4 g/g oil) in a one-liter flask under nitrogen ($N_2$) at room temperature. DHASCO®-T oil is prepared from the microalgae *Crypthecodinium cohnii*. The mixture was allowed to stir for 15 minutes to obtain a homogeneous solution. 67 g of a 21% solution of sodium ethoxide/ethanol (NaOEt/EtOH; approximately 1.04 molar equivalents of triglycerides) was then added to the solution and the mixture was allowed to reflux under $N_2$ for about 9 hours. The progress of the reaction was monitored by gas chromatography (GC) and thin-layer chromatography (TLC). When the reaction was completed, approximately 75 mL of EtOH was removed by distillation. The reaction mixture was then allowed to cool to room temperature under $N_2$. 300 mL hexane was added to the cooled reaction mixture, and the mixture was allowed to stir for 15 minutes at room temperature. 300 mL of deionized water was then added to the mixture, and the mixture was allowed to stir for an additional 15 minutes. After removing and saving the organic layer, the aqueous layer was washed twice with 300 mL portions of hexane. A dark brown aqueous layer was discarded. The combined organic layers were then washed with 200 mL of a saturated NaCl solution. A GC analysis of the organic layer indicated the presence of about 44.7% DHA ethyl ester; the remaining materials were predominantly lower molecular weight ethyl esters (see Table 1).

The combined organic layer was concentrated under reduced pressure. The crude concentrate was then subjected to vacuum fractional distillation. The lower molecular weight ethyl esters were collected at temperatures between 100-150° C. and at a pressure of 0.8 mm Hg. The major components of this fraction were oleic, saturated C-14, and C-12 esters. The DHA ethyl ester was collected at temperatures between 155-165° C. and at a pressure of 0.8 mm Hg. A GC analysis of the DHA ethyl ester fraction showed a purity of about 91.3% DHA (see Table 1). From the fractional distillation, 68 g (86% yield) of the DHA ethyl ester was obtained as a light yellow oil.

TABLE 1

GC Analyses of DHASCO ®-T Oil Transesterification and Distillation Products

| Sample | Organic Layer After Transesterifaction | DHA Ethyl Ester-Containing Fraction After Vacuum Fractional Distillation |
| --- | --- | --- |
| % 22:6 (n-3) DHA | 44.72 | 91.29 |
| % 20:5 (n-3) EPA | 0.00 | 0.00 |
| % Additional components | 55.28 | 8.81 |

Example 2

This example illustrates a method of the present invention for purifying ethyl docosahexaneoate (DHA ethyl ester) from a crude *Crypthecodinium cohnii* oil.

A crude oil obtained from *Crypthecodinium cohnii* by hexane extraction (DHA content of 0.5 g/g oil) was used directly without any further processing, such as winterization and/or RBD processing. 150 mL of absolute ethanol was added to 175 g (approximately 0.2 moles of triglycerides) of the crude oil in a one-liter flask under $N_2$ at room temperature. The mixture was allowed to stir for 15 minutes to obtain a homogeneous solution. 67 g of a 21% solution of NaOEt/EtOH (approximately 1.04 molar equivalents of triglycerides) was then added to the solution, and the mixture was allowed to reflux under $N_2$ for about 10 hours. The progress of the reaction was monitored by GC and TLC. When the reaction was completed, approximately 75 mL of ethanol was removed by distillation, and the mixture was allowed to cool to room temperature under $N_2$. 300 mL of hexane was added to the cooled mixture, and the mixture was allowed to stir for 15 minutes at room temperature. 300 mL of deionized water was then added to the mixture, and the mixture was allowed to stir for an additional 15 minutes. After removing and saving the organic layer, the aqueous layer was washed twice with 300 mL portions of hexane. The combined organic layer was then washed with 200 mL of a saturated NaCl solution. A GC analysis of the organic layer indicated the presence of about 51% DHA ethyl ester; the remaining materials were predominantly lower molecular weight ethyl esters (see Table 2).

The combined organic layer was concentrated under reduced pressure. The crude concentrate was then subjected to vacuum fractional distillation. The lower molecular weight ethyl esters were collected at temperatures between 100-150° C. and at a pressure of 0.8 mm Hg. The major components of this fraction were oleic, saturated C-14, and C-12 esters. The DHA ethyl ester was collected at temperatures between 155-165° C. and at a pressure of 0.8 mm Hg. A GC analysis of the DHA ethyl ester fraction showed a purity of about 92% DHA (see Table 2). From the fractional distillation, 69 g (66% yield) of the DHA ethyl ester was obtained as a light yellow oil.

TABLE 2

GC Analyses of Crude *Crypthecodinium cohnii* Oil Transesterification and Distillation Products

| Sample | Organic Layer After Transesterifaction | DHA Ethyl Ester-Containing Fraction After Vacuum Fractional Distillation |
| --- | --- | --- |
| % 22:6 (n-3) DHA | 51.25 | 91.80 |
| % 20:5 (n-3) EPA | 0.00 | 0.00 |
| % Additional components | 48.75 | 8.20 |

Example 3

This example illustrates a method of the present invention for purifying ethyl docosahexaenoate (as a DHA ethyl ester/DPA ethyl ester mixture) from a crude *Schizochytrium* sp. oil.

A crude oil obtained from *Schizochytrium* sp. by hexane extraction was used directly without any further processing, such as winterization and/or RBD processing.

150 mL of absolute ethanol was added to 175 g (approximately 0.2 moles of triglycerides) of the crude oil (DHA content 40%, DPA content 15%) in a one-liter flask under $N_2$ at room temperature. The mixture was allowed to stir for 15 minutes to obtain a homogeneous solution. 67 g of a 21% solution of NaOEt/EtOH (approximately 1.04 molar equivalents of triglycerides) was then added to the solution, and the mixture was allowed to reflux under $N_2$ for about 10 hours. The progress of the reaction was monitored by GC and TLC. When the reaction was completed, approximately 65 mL of ethanol was removed by distillation, and the mixture was allowed to cool to room temperature under $N_2$. 300 mL of hexane was added to the cooled mixture, and the mixture was allowed to stir for 15 minutes at room temperature. 300 mL of deionized water was then added to the mixture, and the mixture was allowed to stir for an additional 15 minutes. After removing and saving the organic layer, the aqueous layer was washed twice with 300 mL portions of hexane. The combined organic layer was washed with 200 mL of a saturated NaCl solution. A GC analysis of the organic indicated the presence of about 40% DHA ethyl ester and 15% DPA ethyl ester; the remaining materials were predominantly lower molecular weight ethyl esters (see Table 3).

The combined organic layer was concentrated under reduced pressure. The crude concentrate was then subjected to vacuum fractional distillation. The lower molecular weight ethyl esters were collected at temperatures between 100-150° C. and at a pressure of 0.8 mm Hg. The major components of this fraction were saturated C-14, and C-16 ethyl esters. The DHA ethyl ester/DPA ethyl ester mixture was collected at temperatures between 155-170° C. and at a pressure of about 0.5 mm Hg. A GC analysis of the DHA/DPA ethyl ester fraction showed a combined purity of about 93% (see Table 3). From the fractional distillation, 85 g (85% yield) of the DHA/DPA ethyl ester was obtained as a very light yellow oil.

TABLE 3

GC Analyses of Crude *Schizochytrium* sp. Oil Transesterification and Distillation Products

| Sample | Organic Layer After Transesterifaction | DHA/DPA Ethyl Ester-Containing Fraction After Vacuum Fractional Distillation |
|---|---|---|
| % 22:6 (n-3) DHA | 40.07 | 67.31 |
| % 22:5 (n-6) DPA | 15.09 | 25.86 |
| % 20:5 (n-3) EPA | 1.21 | 0.32 |
| % Additional components | 43.63 | 6.5 |

Example 4

This example illustrates GC analyses of crude and purified PUFA ethyl esters from *Crypthecodinium cohnii* oil and *Schizochytrium* sp. oil.

A crude oil obtained from *Schizochytrium* sp. or *Crypthecodinium cohnii* by hexane extraction was used directly without any further processing, such as winterization and/or RBD processing. The crude oils were then subjected to a transesterification reaction as described above in Examples 2 and 3. The crude ethyl esters were then subjected to urea adduction as described above, or to distillation as described in Examples 2 and 3. GC analyses were then performed on each sample along with a DPA ethyl ester product or DHA ethyl ester product (Nu-Chek Prep, Inc., Elysian, Minn.). The results are presented below in Table 4 (*Schizochytrium* sp.) or Table 5 (*Crypthecodinium cohnii*). Two analyses were performed on the crude and distilled ethyl esters from the *Crypthecodinium cohnii* oil.

TABLE 4

GC Analyses of *Schizochytrium* sp. Ethyl Ester Products

| Fatty Acid | Crude Ethyl Esters | Ethyl Esters after Urea Adduction of Crude Oil | Ethyl Esters after Distillation of Crude Oil | Nu-Chek DPA EE |
|---|---|---|---|---|
| % C12:0 | 0.26 | 0.20 | 0.00 | 0.67 |
| % C14:0 | 8.63 | 1.68 | 0.00 | 0.00 |
| % C14:1 | 0.00 | 0.13 | 0.00 | 0.36 |

TABLE 4-continued

GC Analyses of *Schizochytrium* sp. Ethyl Ester Products

| Fatty Acid | Crude Ethyl Esters | Ethyl Esters after Urea Adduction of Crude Oil | Ethyl Esters after Distillation of Crude Oil | Nu-Chek DPA EE |
|---|---|---|---|---|
| % C16:0 | 24.65 | 0.53 | 0.00 | 0.10 |
| % C16:1 | 0.40 | 0.00 | 0.00 | 0.00 |
| % C18:0 | 0.57 | 0.00 | 0.00 | 0.10 |
| % C18:1 (n-9) | 0.36 | 0.00 | 0.00 | 1.77 |
| % C18:1 (n-7) | 0.35 | 0.00 | 0.00 | 0.72 |
| % C18:2 | 0.41 | 0.00 | 0.00 | 0.00 |
| % C18:2 (n-6) | 0.24 | 0.58 | 0.00 | 0.00 |
| % C20:3 (n-6) | 0.42 | 2.75 | 0.00 | 0.00 |
| % C20:3 (n-3) | 0.00 | 0.27 | 0.00 | 0.00 |
| % C20:3 (n-6) | 0.00 | 0.59 | 0.00 | 0.00 |
| % C20:4 ARA | 1.50 | 2.29 | 0.00 | 0.16 |
| % C20:5 (n-3) EPA | 0.00 | 2.01 | 0.00 | 0.00 |
| % C22:4 (n-6) | 0.00 | 0.00 | 0.00 | 3.83 |
| % C22:5 (n-6) DPA | 15.89 | 22.78 | 26.46 | 87.15 |
| % C22:5 (n-3) DPA | | | | 5.21 |
| % C22:6 (n-3) DHA | 40.65 | 57.67 | 71.83 | 0.00 |
| % Additional components | 4.95 | 7.19 | 0.94 | 0.80 |

Example 5

This example illustrates a method of the present invention for purifying ethyl docosahexaneoate (DHA ethyl ester) from a mixture of fatty acid ethyl esters of docosahexaneoic acid-containing single cell oil via urea crystallization.

150 g crude mixture of fatty acid ethyl esters, obtained by transesterification of docosahexaneoic acid-containing single cell DHASCO®-T oil prepared from the microalgae *Crypthecodinium cohnii*, was added to a solution of 262.5 g urea (1.75 wt. eq. of esters) in 1050 mL methanol (7 vol eq of esters) at 70° C. under nitrogen. The resulting mixture of urea and esters was continued to heat at 70° C. under nitrogen for 1 hr. The mixture was first allowed to cool to 20° C. followed by cooling to 0-4° C. to complete the urea adduct crystallization. The mixture was allowed to stand for additional 2 hours at 0-4° C. The crystallized urea adduct was then filtered at 0-4° C.

The filtrate was diluted with 300 mL of water and the mixture was acidified with dilute sulfuric acid to a pH of 1-2. The acidified solution was extracted with 300 mL×3 of hexane. The combined hexane extracts were washed with saturated NaCl solution. The washed hexane solution was dried over anhydrous sodium sulfate and concentrated in vacuo to obtain 70-75% of theoretical yield. Typically, GC analysis showed purity of above obtained DHA Ethyl ester around 90-96% (800-860 mg/g).

TABLE 5

GC Analyses of *Crypthecodinium cohnii* Ethyl Ester Products

| Fatty Acid | Crude Ethyl Esters | Ethyl Esters after Urea Adduction of Crude Oil | Ethyl Esters after Distillation of Crude Oil | Crude Ethyl Esters #2 | Ethyl Esters after Distillation of Crude Oil #2 | Nu-Chek DHA EE |
|---|---|---|---|---|---|---|
| % C8:0 | 0.19 | 0.00 | 0.00 | 0.36 | 0.00 | 0.00 |
| % C10:0 | 0.95 | 0.00 | 0.00 | 1.86 | 0.00 | 0.00 |
| % C12:0 | 4.04 | 0.00 | 0.00 | 7.18 | 0.00 | 0.00 |
| % C13:0 | 0.00 | 0.09 | 0.00 | 0.00 | 0.00 | 0.00 |
| % C14:0 | 13.77 | 0.00 | 0.00 | 19.99 | 0.00 | 0.00 |
| % C14:1 | 0.17 | 0.00 | 0.00 | 0.19 | 0.00 | 0.00 |
| % C16:0 | 11.08 | 0.00 | 0.10 | 16.15 | 0.00 | 0.10 |

TABLE 5-continued

| | | | GC Analyses of *Crypthecodinium cohnii* Ethyl Ester Products | | | |
|---|---|---|---|---|---|---|
| Fatty Acid | Crude Ethyl Esters | Ethyl Esters after Urea Adduction of Crude Oil | Ethyl Esters after Distillation of Crude Oil | Crude Ethyl Esters #2 | Ethyl Esters after Distillation of Crude Oil #2 | Nu-Chek DHA EE |
| % C16:1 | 2.83 | 0.00 | 0.00 | 2.24 | 0.00 | 0.00 |
| % C18:0 | 0.21 | 0.00 | 0.00 | 0.48 | 0.00 | 0.00 |
| % C18:1 (n-9) | 9.77 | 0.00 | 0.00 | 10.27 | 0.00 | 0.00 |
| % C18:1 (n-7) | 0.00 | 0.00 | 0.00 | 0.00 | 0.18 | 0.00 |
| % C22:5 (n-3) DPA | 0.65 | 0.00 | 1.16 | 0.20 | 0.59 | 0.00 |
| % C22:6 (n-3) DHA | 55.64 | 93.00 | 89.67 | 41.26 | 96.73 | 99.95 |
| % C24:0 | 0.00 | 0.00 | 0.69 | 0.00 | 0.00 | 0.00 |
| % C28:8 | 0.60 | ** | 1.40 | 0.25 | 1.20 | 0.00 |
| % Additional components | 0.70 | 2.52 | 8.38 | 0.50 | 1.11 | 0.05 |

** Not Determined

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing best mode of carrying out the invention should be considered exemplary in nature and not as limiting to the scope and spirit of the invention as set forth in the appended claims.

What is claimed is:

1. A composition comprising at least 90 wt. % ethyl ester of docosahexaenoic acid, wherein the composition further comprises at least 0.1 wt. % of docosapentaenoic acid (n-3) or an ester thereof; wherein said composition is from a single microorganism source and said single microorganism is of the genus *Crypthecodinium* or *Schizochytrium*.

2. A composition comprising at least 70 wt. % ethyl ester of docosahexaenoic acid and at least 25 wt. % ethyl ester of docosapentaenoic acid (n-6); wherein said composition is from a single microorganism source and said single microorganism is of the genus *Schizochytrium* or *Thraustochytrium*.

3. A product comprising a composition according to claim 1, wherein said product is selected from baked goods, vitamin supplements, diet supplements, and powdered drinks.

4. A food product comprising a composition according to claim 2.

5. The composition according to claim 2, wherein the microorganism is *Schizochytrium* sp.

6. The composition according to claim 1, wherein the microorganism is *Crypthecodinium cohnii* or *Schizochytrium* sp.

* * * * *